United States Patent [19]

Leveen et al.

[11] Patent Number: 4,820,298

[45] Date of Patent: Apr. 11, 1989

[54] INTERNAL VASCULAR PROSTHESIS

[76] Inventors: Eric G. Leveen, 141 S. Battery, Charleston, S.C. 29401; Robert F. Leveen, 312 Lombard St., Philadelphia, Pa. 19147

[21] Appl. No.: 123,367

[22] Filed: Nov. 20, 1987

[51] Int. Cl.$^4$ .......................... A61F 2/06; A61F 2/02; A61B 17/04

[52] U.S. Cl. .................................... 623/1; 128/331 C; 623/10

[58] Field of Search .............. 128/1 R, 334 C, 334 R, 128/344, 343, 345, 342; 623/1, 10, 11

[56] References Cited

U.S. PATENT DOCUMENTS

| | | | |
|---|---|---|---|
| 4,649,922 | 3/1987 | Wiktor | 128/344 |
| 4,655,771 | 4/1987 | Wallsten | 128/334 R |
| 4,662,885 | 5/1987 | DiPisa, Jr. | 623/1 |
| 4,733,665 | 3/1988 | Palmaz | 623/1 |
| 4,743,251 | 5/1988 | Barra | 623/1 |

FOREIGN PATENT DOCUMENTS 2189150 10/1987 United Kingdom .................... 623/1

*Primary Examiner*—Richard J. Apley
*Assistant Examiner*—David J. Isabella
*Attorney, Agent, or Firm*—John S. Hale

[57] ABSTRACT

A medical stent for use in an aneurysm constructed with a flexible tubular body formed from a medical thermoplastic in the form of a helix. The flexible tubular body defines a lumen and the body is adapted to assume a substantial linear configuration when mounted on a stylet with the material of the body having a recovery memory which causes it to assume a helical configuration when it is removed from the stylet. The body is provided with strands which are connected to adjacent loops of the helix and extend in the space defined by each coil of the helix to allow clot and ingrowth of tissue to seal off the dilated portion of the vessel.

17 Claims, 2 Drawing Sheets

INTERNAL VASCULAR PROSTHESIS

BACKGROUND OF INVENTION

Degeneration or disruption of the connective tissue structures of the arterial wall can cause an artery to undergo extreme dilation, or aneurysm formation. With progression of the dilation, the tension on the vessel wall increases in direct proportion to the dilation, according to LaPlace's law which states that the tension on the wall is directly proportional to the pressure times the radius. Thus, progressive dilation leads to the eventual rupture of the artery because the tension on the vessel wall increases. Beyond a certain diameter, aneurysms are likely to rupture and cause death from internal hemorrhage, and surgical replacement of the artery with a bypass graft is mandated. Such surgical treatment requires major surgery and carries a significant mortality, especially since the patients requiring this surgery are frequently old and debilitated and do not tolerate blood loss. While the majority of aneurysms which require treatment are usually located in the abdominal aorta, a variety of aneurysms do occur in other vessels. Dissecting aortic aneurysms occur in the thoracic aorta. Pseudoaneurysms and mycotic aneurysms may occur in any location and involve any size vessel.

Ideally, the problem would best be treated in elderly acteriosclerotic aneurysms by the percutaneous introduction of a self-anchoring vascular stent which would restore the vascular lumen to normal size and isolate any additional lumen or blood space from the vessel lumen. The stent would require sufficient structural integrity to provide for a framework on which an envelope of semiporous material could be attached or be developed from cellular growth of body tissue. Such a stent would prevent the development of stenosis from cicatrization. In the case of vascular stenosis, the framework itself would dilate the vessel and maintain its internal lumen. Indeed, Maas has shown that a spiral spring can prevent development of stenosis in both experimental animals and humans. Nonetheless, the introduction of Maas' spiral springs requires a core on which the springs can be wound. This core is too large to be introduced via a narrow angiographic catheter and its introduction in itself becomes a major surgical procedure which requires exposure of a major vessel such as the femoral artery through which the core and spring must be introduced via an arteriotomy. Such a procedure would not be useful in vessels having the size of the carotid artery or renal artery, but theoretically might be useful in the treatment of aneurysms of the abdominal aorta. The methods of Dotter or Amplatz utilize a single strand helically wound wire spring which is introduced through an anigographic catheter after straightening the wire. This spiral spring is manufactured from Nitanol which resumes its former shape at the elevated temperatures of the body. These single coiled wire springs do not always follow a single longitudinal axis but veer off in one direction or another and leave the longitudinal axis. Such performance seriously limits the applicability of single strand helical wire springs as an internal vascular stent.

SUMMARY OF THE INVENTION

The present invention sets forth a single helix of thin walled elliptical tubing which straightens from a preformed elliptical configuration to an elongated elliptical cylinder or band when it is extended over a rigid stylet for insertion into an aneurysm. The tubing is provided with flexible strands which join one loop of a spiral to another. When the spiral tube is extended over the stylet, the elastic strands lay flat against the extended tubing making it easier to insert the prosthesis through the femoral artery. When the stylet is removed from the tubing, the tubing assumes its natural spiral configuration and the flexible strands close the space between the spirals allowing clotting and ingrowth of tissue to seal off the aneurysm.

DETAILED DESCRIPTION OF THE DRAWINGS

Figure 1:
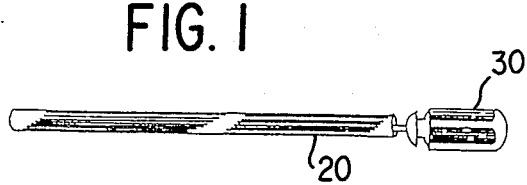
FIG. 1 is a side elevational view of the invention showing it extended over a stylet.
Figure 2:
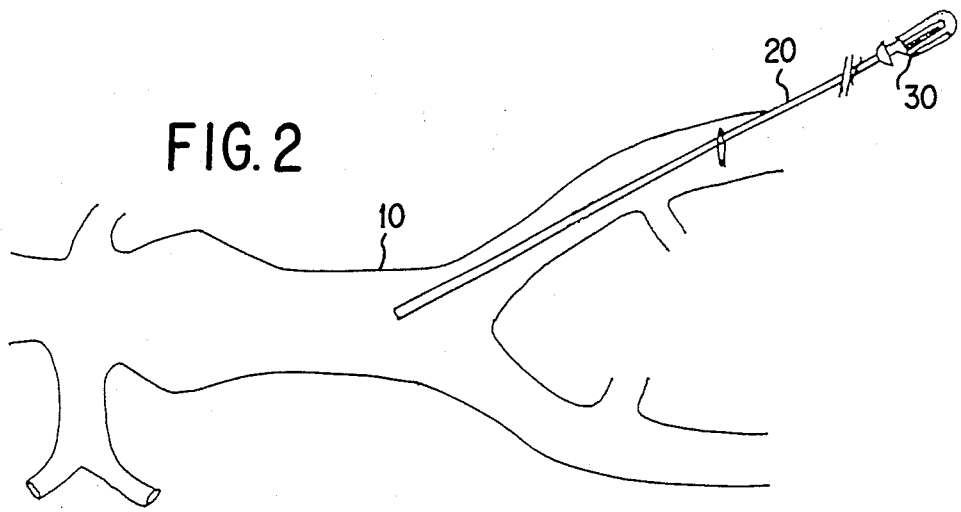
FIG. 2 is a perspective view of the invention showing insertion of a stylet and tubing into an artery.
Figure 3:
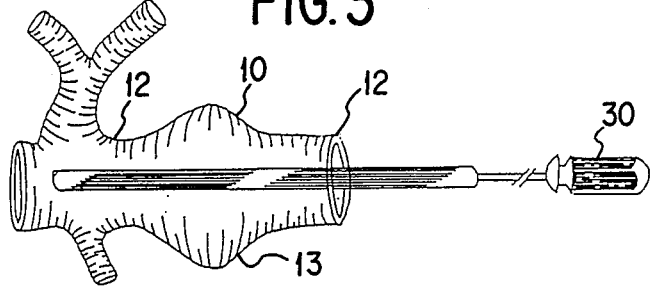
FIG. 3 is a perspective view of the invention of Figure showing placement of the invention in the aneurysm.
Figure 4:
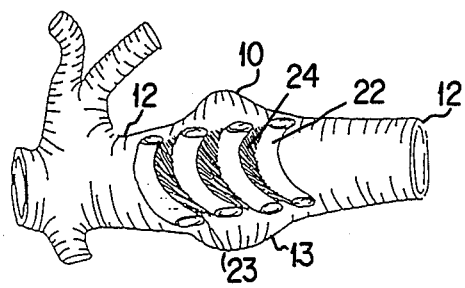
FIG. 4 is a partial cross-sectional view of the inventive tubing with stylet removed forming a helical configuration inserted in place in an aneurysm.
Figure 5:
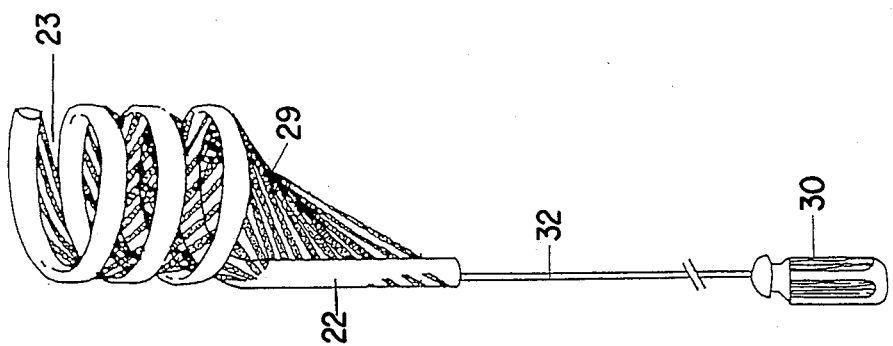
FIG. 5 is a perspective view of the invention with the stylet partially removed and the tubing forming a helical configuration.

The best mode and preferred embodiment is shown in FIGS. 1 through 5. The spiral tubing 20 which is preferably constructed of polycarbonate polyester polycarbonate or other suitable material which is well tolerated by tissues can be introduced percutaneously through an introducing sheath or can be threaded over a coaxial inert angiographic catheter, guide wire or stylet 30. Once the tubing 20 is pushed off the end of the wire 32 of stylet 30 it assumes a performed helical configuration 22 and stent in a vessel 10. The helical tube 22 serves as the skeleton from which flexible strands 24 are attached to join one spiral loop to the other closing the space 23 between the spirals of the helix. This will permit the internal bypass of an aneurysmal dilation of a major artery. The helix or coil in essence connects the two unexpanded portions 12 of the artery 10 while the strands 24 allow clot and ingrowth of tissue to seal off the dilated portion 13 of the vessel. The strands 24 as shown in FIG. 5 are a plurality of single monofilaments, each of which is formed into a coil and stretches. The configuration of the strand is similar to the wire on a telephone hand set.

Figure 6:
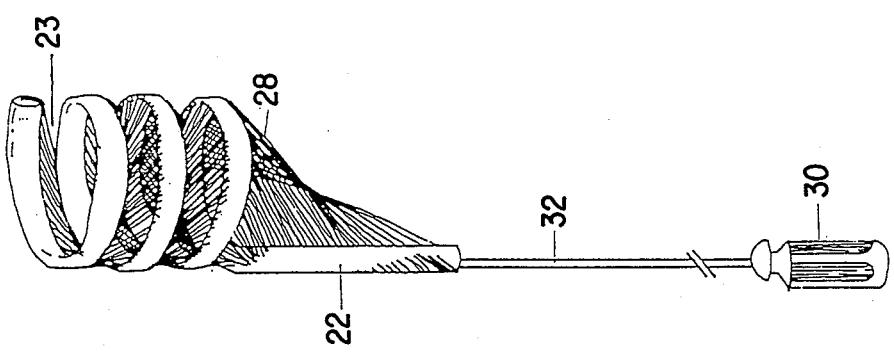
FIG. 6 is a perspective view of another embodiment of the invention with the stylet partially removed and the tubing forming a helical configuration.
Figure 7:
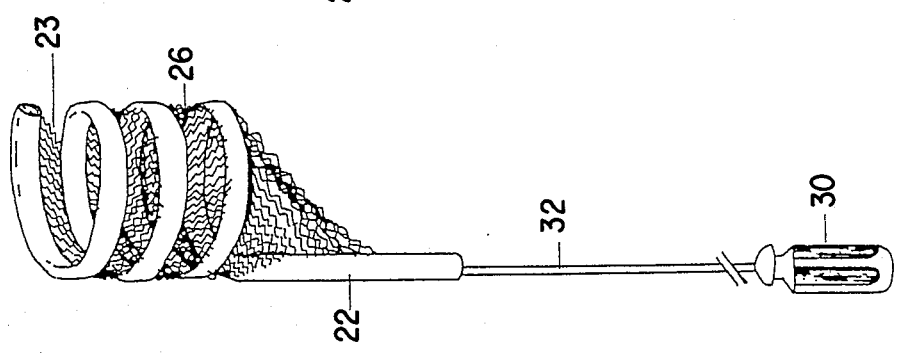
FIG. 7 is a perspective view of yet another embodiment of the invention with the stylet partially removed and the tubing forming a helical configuration.
Figure 8:
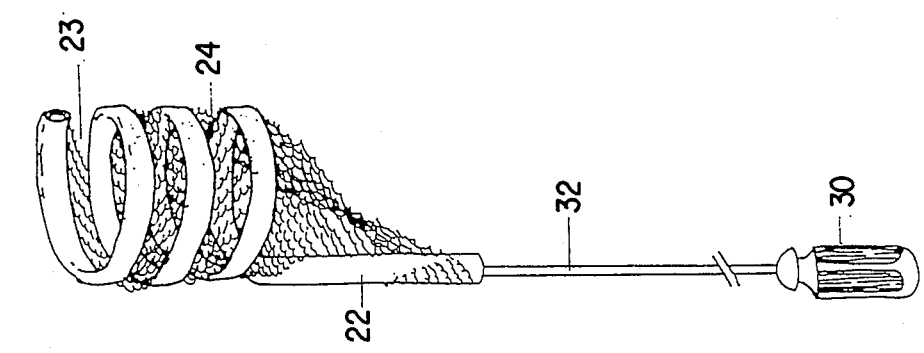
FIG. 8 is a perspective view of still another embodiment of the invention with the stylet partially removed and the tubing forming a helical infringement.

In another embodiment of the invention as shown in FIG. 6, a monofilament strands 26 are used. Each strand zig zags back and forth and takes the configuration of a series of letter Z's strung together. The third embodiment is shown in FIG. 7. In this embodiment, elastomeric strands 28 similar to spandex which is texturized polyurethene is used. Each strand stretches sufficiently to allow it to be extended on a mandril. In yet another embodiment as shown in FIG. 8, a foam material 29 which has elastomeric properties is used. The foam 29 can be a teflon sponge. All of the aforementioned strands follow the direction of the spiral so they have less distance to stretch. Thus it can be seen that flexible strands join one loop of the helix to the adjacent loop. when the spiral tube 20 is extended over the mandril the flexible elastic strands lay flat against the extended tubing making it easier to insert the prothesis through the femoral artery.

The invention allows for the introduction of the helix tube in a longitudinally collapsed form which thereby provides a narrow linear form through an anteriotomy and subsequent controlled expansion into a helix when within the vessel.

The plastic helical coil tubing 20, is formed as a linear extrusion of a thermoplastic with suitable physical characteristics and biological acceptability. One plastic which has been found useful for this purpose is a thermoplastic polyester polycarbonate copolymer. The linear extrusion is then wound around a mandril and reheated to form the helical spring coil. The strand material is sonically welded to appropriate sections of the tubing or alternatively, fastened by suitable adhesive.

The spaces 23 formed between the helical loops are closed by the growth of tissue over the interspaced strands which eventually reconstitutes the vessels interior. The interior of the healed vascular prosthesis has a smooth endothelial appearance of a normal vessel.

While the general embodiments of the present invention have been described, it will be apparent to those of ordinary skill in the art that various alternative configurations and embodiments can readily be adapted to the present invention and are considered to fall within the scope thereof as set forth in the following claims.

What is claimed:

1. A medical stent for use in aneurysms comprising a flexible tubular body defining a lumen and strand means mounted to said tubular body, said tubular body being adapted to assume a substantially linear configuration when mounted on inserter means and constructed of a material having a recovery memory which causes it to expand to a helical configuration when it is removed from said inserter means, said strand means extending substantially between successive coils of the tubular body when in a helical configuration.

2. A medical stent as claimed in claim 1 wherein said strand means is integrally formed with said tubular body.

3. A medical stent as claimed in claim 1 wherein said tubular body is a thermoplastic material.

4. A medical stent as claimed in claim 3 wherein said thermoplastic material is polyester polycarbonate copolymer.

5. A medical stent as claimed in claim 1 wherein said strand means comprises a plurality of monofilament strands formed with a coil shape.

6. A medical stent as claimed in claim 1 wherein said strand means comprises a plurality of monofilament strands formed with a zig zag shape approximating a series of the letters Z strung together.

7. A medical stent as claimed in claim 1 wherein said strand means comprises a plurality of monofilament strands formed of texturized polyurethane.

8. A medical stent as claimed in claim 1 wherein said strand means comprises a plurality of strands formed of a foam with elastomeric properties.

9. A medical stent as claimed in claim 8 wherein said foam is a teflon sponge material.

10. A medical stent as claimed in claim 1 wherein said strand means are flexible and are adapted to lie substantially parallel to the axis of the tubular body when mounted in inserter means.

11. A medical stent as claimed in claim 1 wherein said strand means comprises a plurality of stretchable strands which extend into the space defined between successive coils of said tubular body helical configuration.

12. A medical stent as claimed in claim 1 wherein said strand means forms a wavy configuration when viewed in the space defined between successive coils of the helical configuration of the tubular body.

13. A medical stent for use in aneurysms comprising a flexible tubular body defining a lumen, said tubular body being constructed of thermoplastic material and adapted to assume a substantially linear configuration when mounted on inserter means and constructed with a material having a recovery memory which causes it assume a helical configuration when it is removed from said inserter means and strand means mounted to said tubular body, said strand means comprising a plurality of flexible strands which join one loop of the helical configuration to another loop when the tubular body assumes a helical configuration and lay flat against the tubular body when it is extended into a linear configuration on said insertion means.

14. A method for placing a stent in an aneursym formation in the vessel wall of a blood vessel comprising the steps of:
  (a) inserting a plastic medical stent having a helical configuration in its normal configuration on an inserting means so that said stent forms a linear configuration;
  (b) inserting said stent into a blood vessel so that said stent extends past the aneursym formation in the blood vessel with each end of the stent being placed adjacent the normal wall of the blood vessel; and
  (c) removing the inserting means from said stent and said blood vessel and the allowing the stent to form into a helical configuration with strand means connecting adjacent loops of the helix in said blood vessel.

15. A method as claimed in claim 14 wherein said strand means extends into the space between successive coils when said stent is placed in a blood vessel.

16. A method as claimed in claim 14 wherein said insertion means is a stylet.

17. A method as claimed in claim 14 wherein said insertion means is a wire.

* * * * *